United States Patent
Kanoun-Copy et al.

(10) Patent No.: US 9,452,113 B2
(45) Date of Patent: Sep. 27, 2016

(54) METHOD FOR TREATING OILY SKIN

(71) Applicant: L'OREAL, Paris (FR)

(72) Inventors: Leïla Kanoun-Copy, Savigny sur Orge (FR); Benoit Muller, Paris (FR)

(73) Assignee: L'OREAL, Paris (FR)

(*) Notice: Subject to any disclaimer, the term of this patent is extended or adjusted under 35 U.S.C. 154(b) by 112 days.

(21) Appl. No.: 14/408,166

(22) PCT Filed: Jun. 12, 2013

(86) PCT No.: PCT/IB2013/054805
§ 371 (c)(1),
(2) Date: Dec. 15, 2014

(87) PCT Pub. No.: WO2013/186716
PCT Pub. Date: Dec. 19, 2013

(65) Prior Publication Data
US 2015/0127071 A1 May 7, 2015

Related U.S. Application Data

(60) Provisional application No. 61/694,298, filed on Aug. 29, 2012.

(30) Foreign Application Priority Data

Jun. 13, 2012 (FR) ...................................... 12 55548

(51) Int. Cl.
*A61N 5/06* (2006.01)
*A61K 8/02* (2006.01)
(Continued)

(52) U.S. Cl.
CPC .............. *A61K 8/0279* (2013.01); *A61K 8/25* (2013.01); *A61N 5/0616* (2013.01);
(Continued)

(58) Field of Classification Search
CPC ....................... A61F 9/008; A61F 2009/00872
See application file for complete search history.

(56) References Cited

U.S. PATENT DOCUMENTS

| 4,324,250 A | 4/1982 | Braun et al. |
| 6,183,773 B1 | 2/2001 | Anderson |

(Continued)

FOREIGN PATENT DOCUMENTS

| FR | 2 454 803 A1 | 11/1980 |
| GB | 2 356 570 A | 5/2001 |

(Continued)

OTHER PUBLICATIONS

Dow Corning, "Dow Corning VM-2270 Aerogel Fine Particles," Apr. 2009, pp. 1-5, XP-002650585, http://www2.dowcorning.com/DataFiles/090007c88020e235.

(Continued)

*Primary Examiner* — William Thomson
*Assistant Examiner* — Jeffrey Lipitz
(74) *Attorney, Agent, or Firm* — Oliff PLC (57) ABSTRACT

The present invention relates to a method for the cosmetic (non-therapeutic) treatment of oily skin, including the steps: a) exposing the oily skin to a first quasi-monochromatic light of artificial origin having a dominant wavelength peak between 300 and 700 nm, better still between 400 and 600 nm, even better still between 560 and 620 nm, and in particular of around 590 nm, and b) applying to the oily skin a cosmetic composition comprising at least 1% by weight of hollow particles and preferably from 2% to 6% by weight of hollow particles, relative to the total weight of said composition, the hollow particles being hydrophobic silica aerogel particles.

15 Claims, 2 Drawing Sheets

(51) Int. Cl.
*A61K 8/25* (2006.01)
*A61Q 19/00* (2006.01)
*A61N 5/067* (2006.01)

(52) U.S. Cl.
CPC ...... *A61Q 19/008* (2013.01); *A61K 2800/412* (2013.01); *A61K 2800/612* (2013.01); *A61K 2800/81* (2013.01); *A61N 2005/067* (2013.01); *A61N 2005/0651* (2013.01); *A61N 2005/0653* (2013.01); *A61N 2005/0654* (2013.01); *A61N 2005/0659* (2013.01); *A61N 2005/0661* (2013.01); *A61N 2005/0663* (2013.01); *A61N 2005/0667* (2013.01)

(56) References Cited

U.S. PATENT DOCUMENTS

| | | |
|---|---|---|
| 6,600,951 B1 | 7/2003 | Anderson |
| 2005/0055070 A1 | 3/2005 | Jones et al. |
| 2006/0067868 A1* | 3/2006 | Kutsovsky ............... A61K 8/11 423/335 |
| 2006/0200213 A1* | 9/2006 | McDaniel ............ A61B 18/203 607/89 |
| 2006/0212025 A1 | 9/2006 | McDaniel |
| 2009/0299268 A1 | 12/2009 | Anderson |

FOREIGN PATENT DOCUMENTS

| | | |
|---|---|---|
| WO | WO 03/086215 A1 | 10/2003 |
| WO | WO 2012/027728 A2 | 3/2012 |

OTHER PUBLICATIONS

Written Opinion issued in French Application No. FR 12 55548 dated Mar. 7, 2013 (with translation).

International Search Report issued in International Application No. PCT/IB2013/054805 mailed Apr. 24, 2014.

Written Opinion of the International Searching Authority issued in International Application No. PCT/IB2013/054805 mailed Apr. 24, 2014.

* cited by examiner

METHOD FOR TREATING OILY SKIN

The present invention relates to the cosmetic, i.e. non-therapeutic, treatment of oily skin.

The skin is rich in sebaceous glands and is continually renewed. The secretion of sebum is a normal phenomenon which is useful to both the skin and the head of hair. Sebum is normally an agent for moisturizing the epidermis. It is the natural product of the sebaceous gland, which is an annex of the pilosebaceous unit. It is essentially a more or less complex mixture of lipids. Sebum protects the skin and also the scalp and gives the hair sheen by lubricating the cuticle.

Unfortunately, a hypersecretion of sebum, or seborrhoea, may lead to aesthetic disorders. Thus, an excessive secretion of sebum may result in oily skin with a shiny or glistening appearance and it may also promote the appearance of an oily dandruff condition of the scalp or oily dandruff. It may be accompanied by an increase in pore size. For example, stress, fatigue and the winter period may be factors that intensify these conditions in the majority of people. Among the population having oily skin, it is possible to find subjects who have endocrine disorders or neurological disorders, or obese subjects. It is also possible to find adolescents, people suffering from excess hormones (in particular male hormones), menstruating women or menopausal women who have oily skin.

There is therefore a need to overcome these problems by providing a method for treating oily skin. To combat hyperseborrhoea, the prior art has already proposed various compounds, which, by topical application to the skin, are capable of reducing the lipogenesis of the sebocytes and consequently of limiting the production of sebum. The treatments currently available for hyperseborrhoea are not entirely satisfactory, in particular with regard to the side effects that are frequently associated therewith, such as irritant effects with certain topical agents such as retinoids and benzoyl peroxides.

Methods for treating acne, which aim to reduce the proliferation of *P. acnes*, are known from patent applications US 2006/0212025 and US 2006/0200213.

Presented in U.S. Pat. Nos. 6,183,773 and 6,600,951 are methods for treating disorders of the sebaceous gland by means of light emitted by a laser.

Application US 2009/0299268 has the objective of treating acne. The treatment makes it possible to reduce the secretion of sebum and gives rise to the eradication of the bacteria.

Application GB 2 356 570 teaches treating acne by the emission of light at three different wavelengths, namely within the following ranges: 365-465 nm, 585-645 nm and 646-710 nm.

Finally, application US 2005/0055070 relates to the treatment of acne by light in order to destroy the bacteria, owing to the stimulation of the production of free radicals via a photochemical reaction.

Acne is the main one of the most common forms of dermatosis. It is most common at the age of puberty. It is linked to the proliferation of certain local germs such as *Propionibacterium acnes* (*P. acnes*). Acneic and acne-prone individuals usually have oily, oily-prone or combination skin.

The invention aims to treat oily skin by providing a method for the cosmetic (non-therapeutic) treatment of oily skin, comprising the steps consisting in:

a) exposing the oily skin to a first quasi-monochromatic light of artificial origin having a dominant wavelength peak between 300 and 700 nm, better still between 400 and 600 nm, even better still between 560 and 620 nm, and in particular of the order of around 590 nm, and b) applying to the oily skin a cosmetic composition comprising at least 1% by weight of hollow particles and preferably from 2% to 6% by weight of hollow particles, relative to the total weight of said composition, the hollow particles being hydrophobic silica aerogel particles.

In one embodiment, a subject of the invention is a method for the cosmetic (non-therapeutic) treatment of oily skin, comprising the steps consisting in:

a) exposing the oily skin to a first quasi-monochromatic light of artificial origin having a dominant wavelength peak between 300 and 700 nm, better still between 400 and 600 nm, even better still between 560 and 620 nm, and in particular of the order of around 590 nm, and b) applying to the oily skin a cosmetic composition comprising at least 1% by weight of hollow particles and preferably from 2% to 6% by weight of hollow particles, relative to the total weight of said composition, the hollow particles having a specific surface area per unit of mass of greater than 600 $m^2/g$ and a size, expressed as volume average diameter, ranging from 5 to 30 µm.

The treatment according to the invention, comprising both exposure to light and the application of a composition, has a positive effect on reducing the pore size and decreasing the shininess of the skin. It makes it possible to improve the mattness of the skin earlier in the course of the treatment.

The hydrophobic silica aerogel particles can have a surface effect making it possible to decrease the sheen of the skin and to reduce the appearance of the pore size, for example by limiting the impact of perspiration on the skin.

The wear properties over time of the colour, the matting effect and/or the homogeneity of the deposit of the composition on the skin may thus be improved.

In addition, the exposure to the light may make it possible to prolong the action of the composition on the skin during the day.

Moreover, the application of the composition to the skin makes it possible to compensate for the period of time required for the light to exert its effect. Thus, the user may have the impression that the exposure to the light has an immediate effect, which may make it possible to encourage said user to persevere in the treatment a) of exposure of the oily skin to the light.

Step b) can take place before, after or during step a). Step b) can in particular be carried out during the hour preceding or during the hour following the exposure to the light. It is possible not to apply, to the treated region, any product other than the composition according to the invention, in particular in the hour preceding and/or in the hour following the exposure to the light.

In one preferred embodiment of the invention, step b) is carried out after step a), in particular during the hour following the exposure to the light, or even during the half hour following the exposure to the light.

The expression "monochromatic light" is understood to mean light which consists only of a single wavelength. According to the invention, the expression "quasi-monochromatic light" is understood to mean light emitting a spectrum of wavelengths having a dominant peak at one wavelength. According to the invention, this peak has a spectral width at mid-height of at most ±50 nm and a spectral width at the base of at most ±100 nm. The spectral width at mid-height is defined as the width of the spectrum at half of the power of the dominant peak. The spectral width at the base is defined as the width of the spectrum at 10% of the power of the dominant peak.

The term "skin" denotes the skin of the face, of the body and the scalp. The skin treated may or may not be wrinkled. The skin treated may or may not be acneic.

The skin treated may be non-acneic oily skin. The applicant has observed that it is possible to thus treat skin types which have not developed a clinical manifestation of acne in order to make the skin less oily, less glistening and less shiny.

The expression "non-acneic skin" denotes healthy skin free of the clinical manifestations of acne, such as the presence of numerous acne pimples. In other words, over the whole region of skin exposed to the light with the method according to the invention, the skin is not clinically acneic. The entire region of skin exposed to the light is free of a region that has developed acne. The expression "clinical manifestations of acne" is understood to mean the presence on the skin of acne lesions.

Hyperseborrhoeic oily skin is characterized by an exaggerated secretion and excretion of sebum. The expression "oily skin" denotes skin which obtains a score of greater than 95 $\mu g/cm^2$ on the sebumeter. The expression "very oily skin" denotes a score on the sebumeter of greater than 120 $\mu g/cm^2$ and the expression "excessively oily skin" denotes a score on the sebumeter of greater than 140 $\mu g/cm^2$.

Such skin is also often associated with a lack of desquamation, a glistening complexion, a thick skin texture, enlarged pores or an irregular relief, which manifestations are perceived as being skin imperfections or aesthetic defects. The appearance and/or visibility of the pores is also a characteristic of oily skin. The shininess of the skin is also linked to the enlargement of the pores. Oily skin is also characterized by glistening skin, sometimes of oily appearance, which is thick, having enlarged pilosebaceous pores.

Sebumeter

The sebumeter makes it possible to measure the production of sebum over time. The amount of sebum excreted at the surface of the skin is evaluated using a Sebumeter® SM180 (Courage & Khazaka).

This is a photometric method. A tape of synthetic material, which becomes transparent on contact with the absorbed lipids, is applied to the measurement region for precisely 30 seconds.

Its transparency then increases proportionally with the amount of sebum of the hydrolipid film with which it is in contact.

A recording by reflectometry makes it possible to quantify the increase in transmitted light and thus to determine the total mass of lipids excreted per unit of surface area (in $\mu g \cdot cm^{-2}$).

A measurement on the forehead after careful defatting with 70° alcohol is performed.

Half an hour later, a new measurement is taken. The amount of sebum excreted per unit of surface area and per unit of time may thus be calculated.

The amount of sebum may also be evaluated using a Sebutape®.

Sebutape®

Sebutape® makes it possible to measure the amount of sebum produced over a given period. Use is made of a Sebutape® with the reference S100 from the company CuDerm Corp. TX, USA, also available from the company Monaderm. The Sebutape® is applied and gently pressed on the skin at the temples after careful defatting with 70° alcohol, and left in place in contact with the skin for a time of 30 minutes. Next, the Sebutape® is removed and then brought into contact with a transparent plastic film. The score is determined visually using an appropriate scale of 0 to 5.

Typically, oily skin according to the invention has a score of greater than 2.

Dermascore

The Dermascore makes it possible to visualize certain characteristics of the skin as a function of the polarization of light, namely the pores of the skin with parallel-polarized light and the colour of the skin and also the heterogeneities of the skin with perpendicular-polarized light. Images are captured and an analysis carried out by comparison with the images from an atlas.

The present invention makes it possible to reduce the secretion of sebum. Oily skin is also often associated with a lack of desquamation, a glistening complexion, a thick skin texture and an increased pore size, which manifestations are perceived as being aesthetic disorders which the treatment according to the invention also aims to rectify.

The treatment according to the invention advantageously makes it possible to prevent and/or treat the glistening appearance of the skin. For the purposes of the present invention, the term "preventing" is understood to mean at least partly reducing the risk of manifestation of a given phenomenon. Partial reduction implies that the risk remains but to a lesser degree than before the implementation of the invention.

The treatment in accordance with the invention advantageously makes it possible to prevent and/or treat skin of blotchy, dull and/or uneven, waxy or yellowish appearance, or even of morbid appearance.

The treatment in accordance with the invention advantageously makes it possible to prevent and/or treat the aesthetic disorders associated with an oily scalp, such as a hypersecretion of sebum, or seborrhoea, which may promote the appearance of an oily dandruff condition of the scalp or oily dandruff.

The treatment according to the invention may thus prove to be very particularly effective:
  for preventing and/or treating oily skin,
  for improving the comfort of oily skin and scalps,
  for treating and/or preventing and/or avoiding aesthetic disorders of the scalp associated with excessive excretions and/or secretions of sebum,
  for preventing and/or treating oily scalps, and in particular the oily dandruff conditions of the scalp,
  for re-establishing a balanced ecoflora of the oily scalp.

One hypothesis put forward for explaining the effect of the treatment, without being bound by this explanation, is that the treatment according to the invention acts on the sebaceous gland, decreasing its activity.

The method may have an effect on the physiological and clinical signs of oily skin, in particular the quantity of sebum and the sebum quality. Another effect of the treatment method according to the invention may be to reduce the size of the pores. Yet another effect may be to reduce the visibility of acne scars.

The treatment according to the invention does not aim to destroy the *P. acnes* bacterium. The method makes it possible to reduce the production of sebum by at least 8% and to significantly reduce, by at least 7%, *P. acnes* by a modification of the nutritional conditions for the growth of *P. acnes*. The method according to the invention may make it possible to limit the growth of *P. acnes*. The method according to the invention may make it possible to reduce the population of *P. acnes*, considering the reduction in the presence of oil on the skin, which tends to promote the proliferation of the bacterium. The reduction in the amount of *P. acnes* present on the skin may lead to the reduction in the risk of the occurrence of small acne pimples and also a reduction in sebum production in so far as the presence of *P. acnes* in excess tends to promote sebum production.

The method according to the invention is more particularly intended for treating individuals who are between 20 and 60 years old, better still between 25 and 50 years old, when their skin does not suffer from acne.

Exposure to Light

The method according to the invention may be carried out by exposing the face, by region or in its entirety, the oily scalp, by region or in its entirety, or the body or a part of the body having an oily skin problem, to the light source.

The method according to the invention may be carried out by exposing the face, by region or in its entirety, the oily scalp, by region or in its entirety, or the body or a part of the body, to the light source with a static apparatus that may or may not be in contact with the region treated. The expression "static apparatus" is understood to mean that an apparatus does not have to be moved with respect to the face or the head.

As a variant, the apparatus may be used successively over several regions in order to cover a wider treatment area. Over each region, the apparatus is kept immobile.

The method according to the invention may be carried out with a support that emits light according to the invention, in contact with the skin of the face, of the scalp or of the body. The support may be a material that emits light. The support may be at least partially, or even completely, made of a textile. The method according to the invention may be carried out by a touch-control apparatus, a rigid or flexible screen, a mirror, a housing or a glass that emits light according to the invention.

The treatment does not cause thermal lesions, since the light power is weak.

The spectrum of the light emitted may comprise a first quasi-monochromatic light corresponding to the first light above, alone or in combination with one or more other quasi-monochromatic lights.

Besides the exposure to the first quasi-monochromatic light as defined above, it is possible to expose the oily skin to a second quasi-monochromatic light of artificial origin having a dominant wavelength peak between 700 and 1000 nm, better still between 800 and 900 nm, for example of the order of 870 nm. This second light is between red and infrared. The exposure to the red or infrared light may be carried out simultaneously with or successively to the exposure to the first light mentioned above.

The source producing the red or infrared light may be the same as or different from the source producing the first light mentioned above. It is possible to carry out the treatment using a single light source configured to emit two different quasi-monochromatic lights. As a variant, it is possible to carry out the treatment using two different sources that emit two different quasi-monochromatic lights. The two sources may be activated simultaneously or successively.

It is also possible to expose the skin to a third quasi-monochromatic blue light, having a dominant wavelength peak between, for example, 400 and 450 nm, in particular of the order of 410 to 420 nm. This third additional light may be emitted by a light source different from the light source(s) emitting the first light and optionally the second red or infrared light.

The first light may be dominant with respect to the other light(s). The dominant wavelength peak of the first light may have an intensity greater than the other dominant wavelength peak(s) of the other lights. The first light may, for example, represent more than 50%, better still more than 60% and even better still more than 70% of the total energy of all the light received.

The light source(s) generating the light to which the skin is exposed may comprise at least one of the following: an LED, an LED matrix, an OLED, a laser, an incandescent lamp equipped with a dichroic filter, this list not being limiting.

The use of an OLED may be preferred in so far as they make it possible to apply the light as close as possible to the skin. They may be integrated into a mask or a patch.

The light source(s) may comprise at least one quasi-monochromatic LED. The expression "quasi-monochromatic LED" denotes an LED having an emission spectrum that comprises a dominant wavelength peak with a spectral width at mid-height of at most ±50 nm and a spectral width at the base of the peak of at most ±100 nm. As a variant, the light source may comprise at least one dichromatic LED, that is to say the emission spectrum of which comprises several quasi-monochromatic lights, for example two quasi-monochromatic lights, for example one quasi-monochromatic light for which the dominant peak is between 560 nm and 620 nm, of higher intensity, and one quasi-monochromatic light for which the dominant peak is between 700 nm and 1000 nm, of lower intensity.

The light source(s) may be other than a laser.

The light, in particular the first light having a wavelength between 300 and 700 nm as defined above, may be pulsed. The optional second and/or third lights may also be pulsed, for example with pulses of the same duration and interpulse intervals of the same duration as the first light. As a variant, the pulsation characteristics of these three lights may differ from one another. In another variant, at least one of the second and third lights may be continuous. The pulses may have a duration of between 100 and 500 ms, better still between 200 and 300 ms, for example of the order of 250 ms. The light may be pulsed with interpulse intervals having a duration of between 50 and 200 ms, better still between 70 and 150 ms, for example of the order of 100 ms.

As a variant, all the light emitted may be continuous.

The surface power density of the light received by the oily skin during a treatment may be less than 40 mW/cm$^2$, preferably between 1 and 20 mW/cm$^2$, better still between 1 and 10 mW/cm$^2$, for example of the order of 5 mW/cm$^2$.

The surface energy density received by the oily skin during the treatment, over one day, may be less than 4 J/cm$^2$, better still between 20 mJ/cm$^2$ and 1 J/cm$^2$, for example of the order of 175 mJ/cm$^2$.

It is possible to expose one and the same region of oily skin to the light in accordance with the invention for a duration of less than 20 minutes, for example between 20 and 100 seconds, for example of the order of 35 seconds or of 70 seconds.

In one example of the implementation of the invention, when the skin is positioned at a distance between 0 and 10 cm from the light source, the surface power density received is less than 40 mW/cm$^2$ and the surface energy density received less than 4 J/cm$^2$.

It is possible to carry out said treatment at least once a day, at least one day per week, better still two days per week, or as a variant five days per week, or even every day, for a period of at least two weeks.

In one example of the implementation of the invention, said treatment is carried out at least once a week for a duration of between two and twelve weeks.

The skin thus treated may be oily, very oily, or even excessively oily, as defined above.

The treatment may be carried out on the skin of a subject after evaluating the skin of this subject, the evaluation having made it possible to determine the "oily" nature of the subject's skin. The evaluation may result from a measurement carried out on the subject's skin, for example using a Sebumeter™ or a Sebutape™, or else by self-evaluation. The self-evaluation may, for example, result from responses given by the subject to a detailed questionnaire regarding sensations of oily skin or of glistening skin, or visual observations of the state of his or her skin under various observation conditions, for example at certain moments of the day or a certain time after washing.

The treatment may be carried out with a light having a power of the dominant wavelength in the range 700 nm-1000 nm that is less than at least one quarter of the power of the dominant wavelength in the range 560 nm-620 nm.

Another subject of the invention is, independently or in combination with the aforegoing, a method for the cosmetic treatment of oily skin, in which step a) above is replaced with step a) below:

a) exposing the oily skin, in particular the non-acneic oily skin, to a light source having a dominant wavelength between 300 and 700 nm, better still between 400 and 650 nm, better still between 560 and 620 nm, preferably of the order of 590 nm so as to reduce the production of sebum by at least 8% and so as to reduce the *P. acnes* by at least 7% by a modification of the nutritional conditions for the growth of *P. acnes*.

Composition

The composition may be a cosmetic composition, in particular a care, hygiene and/or makeup cosmetic composition for a keratin material. A composition of the invention is in particular a composition intended to be applied to a keratin material, in particular the skin and more particularly facial skin.

The composition according to the invention contains a cosmetically acceptable medium, i.e. a medium which is compatible with the skin, the nails, the mucous membranes, the tissues and the hair, with no unpleasant odour, colour or appearance, and which does not cause any stinging, tautness or redness which is unacceptable to the user.

Preferably, said medium comprises water and/or one or more cosmetically acceptable organic solvents. The organic solvents can be chosen from linear or branched $C_1$-$C_6$ monoalcohols, such as ethanol, isopropanol, tert-butanol or n-butanol; polyols such as glycerol, propylene glycol, hexylene glycol (or 2-methyl-2,4-pentanediol) and polyethylene glycols; polyol ethers, for instance dipropylene glycol monomethyl ether; and mixtures thereof.

Preferably, the cosmetic composition used according to the invention comprises an amount of organic solvents ranging from 0.05% to 60%, preferably from 0.5% to 50% and even better still from 1% to 40% by weight, relative to the total weight of the cosmetic composition.

According to one preferred embodiment of the invention, the composition has a pH preferably close to that of the skin, between 4 and 7.

The compositions according to the invention may be provided in all the formulation forms conventionally used for a topical application and in particular in the form of aqueous or aqueous-alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be lipid vesicles of ionic and/or non-ionic type (liposomes, niosomes or oleosomes). These compositions are prepared according to the usual methods.

In addition, the composition according to the invention may be more or less fluid and may have the appearance of a white or coloured cream, an ointment, a milk, a lotion, a serum, a paste, a foaming gel, a care product, a tonic or a foam. It can optionally be applied to the skin in aerosol form. It can also be in solid form, for example in the form of a stick.

1—Hydrophobic Silica Aerogel Hollow Particles

The presence of hollow particles is particularly advantageous with regard to the objectives under consideration in the invention.

With regard to their porous nature, these particles have a capacity for absorbing liquid, which makes it possible to absorb the rest of the liquid composition and thus to contribute towards the thickening of the composition containing them.

Their presence also allows a solid anhydrous composition to have good stability over time without exudation of liquid, in particular of oil.

Moreover, the oil-absorbing capacity of hollow particles in accordance with the invention is advantageously greater than 300 ml/100 g and preferably greater than 500 ml/100 g or better still greater than 1000 ml/100 g. This capacity may in particular be characterized by the "wet point" method outlined in detail in the following chapter relating to hydrophobic silica aerogel particles.

For the purposes of the invention, the term "particle" is understood to mean a solid material that is insoluble in an aqueous phase or in a fatty phase and that has a mean size of between 0.5 and 50 µm, preferably between 1 and 30 µm and better still between 5 and 30 µm.

The hydrophobic silica aerogel particles may be present in the composition according to the invention in a content ranging from 0.05% to 15% by weight, preferably from 0.1% to 10% by weight and more preferably from 2% to 6% by weight relative to the total weight of the composition.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science: New York: Academic Press, 1990.

The hydrophobic silica aerogel particles that may be used in the present invention have a specific surface area per unit of mass ($S_M$) greater than 600 $m^2$/g, or even ranging from 600 to 1500 $m^2$/g, preferably from 600 to 1200 $m^2$/g and better still from 600 to 800 $m^2$/g, and a size, expressed as the volume average diameter (D[0.5]), ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles that may be used in the present invention have a size, expressed as the volume average diameter (D[0.5]), ranging from 5 to 30 µm, preferably from 5 to 25 µm, better still from 5 to 20 µm and even better still from 5 to 15 µm.

The specific surface area per unit of mass can be determined by the nitrogen absorption method, known as the BET (Brunauer-Emmett-Teller) method, described in "The Journal of the American Chemical Society", Vol. 60, page 309, Feb. 1938 and corresponding to the international standard ISO 5794/1 (appendix D). The BET specific surface area corresponds to the total specific surface area of the particles under consideration.

The sizes of the hydrophobic silica aerogel particles may be measured by static light scattering using a commercial particle size analyzer such as the MasterSizer 2000 from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., "Light Scattering by Small Particles", Chapters 9 and 10, Wiley, New York, 1957.

According to one advantageous embodiment, the hydrophobic silica aerogel particles that may be used in the present invention have a specific surface area per unit of mass ($S_M$) of greater than 600 m$^2$/g, better still ranging from 600 to 800 m$^2$/g, and a size, expressed as the volume average diameter (D[0.5]), ranging from 5 to 30 µm, better still from 5 to 20 µm and even better still from 5 to 15 µm.

The hydrophobic silica aerogel particles used in the present invention may advantageously have a tapped density p ranging from 0.04 g/cm$^3$ to 0.10 g/cm$^3$ and preferably from 0.05 g/cm$^3$ to 0.08 g/cm$^3$.

In the context of the present invention, this density, known as the tapped density, can be assessed according to the following protocol:

40 g of powder are poured into a measuring cylinder; the measuring cylinder is then placed on the Stay 2003 machine from Stampf Volumeter; the measuring cylinder is subsequently subjected to a series of 2500 tapping actions (this operation is repeated until the difference in volume between 2 consecutive tests is less than 2%); and then the final volume Vf of tapped powder is measured directly on the measuring cylinder. The tapped density is determined by the ratio m/Vf, in this instance 40/Vf (Vf being expressed in cm$^3$ and m in g).

According to one embodiment, the hydrophobic silica aerogel particles that may be used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: $S_V = S_M \cdot \rho$ where $\rho$ is the tapped density expressed in g/cm$^3$ and $S_M$ is the specific surface area per unit of mass expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. At this point, the oil is added one drop at a time and the mixture is then triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The hydrophobic silica aerogel particles that may be used according to the present invention are preferably of silylated silica type (INCI name: silica silylate).

The term "hydrophobic silica" is understood to mean any silica of which the surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

The hydrophobic silica aerogel particles may be surface-modified with trimethylsilyl groups.

As regards the preparation of hydrophobic silica aerogels particles that have been surface-modified by silylation, reference may be made to document U.S. Pat. No. 7,470,725.

Use will in particular be made of the particles of aerogel of hydrophobic silica surface-modified with trimethylsilyl groups.

As hydrophobic silica aerogel particles that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g (oil uptake equal to 1080 ml/100 g).

Advantageously, the hollow particles in accordance with the invention are at least partly formed from hydrophobic silica aerogel particles, preferably those with a specific surface area per unit of mass ($S_M$) ranging from 600 to 1500 m$^2$/g and preferably from 600 to 1200 m$^2$/g, and a size, expressed as the volume average diameter (D[0.5]), ranging from 1 to 1500 µm, better still from 1 to 1000 µm, preferably from 1 to 100 µm, in particular from 5 to 30 µm, more preferably from 5 to 25 µm, better still from 5 to 20 µm and even better still from 5 to 15 µm.

2—Oil

The composition according to the invention may comprise at least one fatty phase that is liquid at ambient temperature and atmospheric pressure, and in particular at least one oil as mentioned below.

Specifically, the presence of an oil is advantageous insofar as it facilitates the dry application of the composition and affords emollience when the composition is emulsified with water.

For the purposes of the present invention, the term "oil" is understood to mean a water-immiscible non-aqueous compound that is liquid at ambient temperature (25° C.) and atmospheric pressure (760 mmHg).

As oils that may be used in the composition of the invention, examples that may be mentioned include:

- hydrocarbon-based oils of animal origin, such as perhydrosqualene;
- hydrocarbon-based oils of vegetable origin, such as liquid triglycerides of fatty acids comprising from 4 to 10 carbon atoms, such as heptanoic or octanoic acid triglycerides, or alternatively, for example, sunflower oil, maize oil, soybean oil, squash oil, grapeseed oil, sesame seed oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil and shea butter oil;
- synthetic esters and ethers, in particular of fatty acids, for instance the oils of formulae R'COOR2 and R'OR2 in which R' represents a fatty acid residue containing from 8 to 29 carbon atoms and R2 represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate or fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;
- linear or branched hydrocarbons of mineral or synthetic origin, such as volatile or non-volatile liquid paraffins, and derivatives thereof, petroleum jelly, polydecenes, and hydrogenated polyisobutene such as Parleam oil;
- fatty alcohols having from 8 to 26 carbon atoms, such as cetyl alcohol, stearyl alcohol and the mixture thereof (cetearyl alcohol), octyldodecanol, 2-butyloctanol, 2-hexyldecanol, 2-undecylpentadecanol, oleyl alcohol or linoleyl alcohol;
- partially hydrocarbon-based and/or silicone-based fluoro oils, for instance those described in document JP-A-2-295 912;
- silicone oils, for instance volatile or non-volatile polymethylsiloxanes (PDMS) with a linear or cyclic silicone chain, which are liquid or pasty at ambient temperature, in particular cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;
- mixtures thereof.

In the list of the abovementioned oils, the term "hydrocarbon-based oil" is understood to mean any oil predominantly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-$C_{1-4}$-alkyl dimethicone and trifluoropropyl dimethicone; and silicone elastomers, for instance the products sold under the name KSG by the company Shin-Etsu, under the names Trefil, BY29 or EPSX by the company Dow Corning, or under the name Gransil by the company Grant Industries.

These fatty substances can be chosen in a varied manner by those skilled in the art so as to prepare a composition having the desired properties, for example of consistency or texture.

According to one particular embodiment of the invention, the composition according to the invention is a water-in-oil (W/O) or, according to one preferred embodiment, oil-in-water (O/W) emulsion. The proportion of the oily phase of the emulsion may range from 5% to 80% by weight and preferably from 5% to 50% by weight relative to the total weight of the composition.

The emulsions generally contain at least one emulsifier chosen from amphoteric, anionic, cationic or non-ionic emulsifiers, used alone or as a mixture, and optionally a co-emulsifier. The emulsifiers are appropriately chosen according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol, sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90R by the company Goldschmidt. A crosslinked elastomeric solid organopolysiloxane comprising at least one oxyalkylene group, such as those obtained according to the procedure of Examples 3, 4 and 8 of the document U.S. Pat. No. 5,412,004 and of the examples of the document U.S. Pat. No. 5,811,487, in particular the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include non-ionic emulsifiers such as oxyalkylenated (more particularly polyoxyethylenated) fatty acid and glycerol esters; oxyalkylenated fatty acid and sorbitan esters; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

3—Other Components which May be Contained in the Composition

The composition according to the invention may also contain attachments which are customary in the cosmetic field, such as hydrophilic or lipophilic gelling agents, preservatives, water, solvents, fragrances, fillers, UV-screening agents, odour absorbers, colorants, basic agents, acids, or non-ionic, anionic or cationic surfactants.

The amounts of these various adjuvants are those conventionally used in the field under consideration, for example from 0.01% to 20% of the total weight of the composition. Depending on their nature, these adjuvants may be introduced into the fatty phase, into the aqueous phase and/or into the lipid vesicles.

As fillers that may be used in the composition of the invention, examples that may be mentioned, besides pigments, include silica powder; talc; polyamide particles and in particular those sold under the name Orgasol by the company Atochem; polyethylene powders; microspheres based on acrylic copolymers, such as those made of ethylene glycol dimethacrylate/lauryl methacrylate copolymer sold by the company Dow Corning under the name Polytrap; expanded powders such as hollow microspheres and in particular the microspheres sold under the name Expancel by the company Kemanord Plast or under the name Micropearl F 80 ED by the company Matsumoto; silicone resin microbeads such as those sold under the name Tospearl by the company Toshiba Silicone; and mixtures thereof.

As hydrophilic or lipophilic gelling agents, mention may in particular be made of carbopols, luvigels, Hostacerin AMPS, Simulgel, Sepigels, xanthan gum, guar gum, cellulose gum, alginates, and mixtures thereof. Mention may also be made of hectorites.

Needless to say, those skilled in the art will take care to select this or these optional additional ingredients and/or active agents, and/or the amount thereof, such that the advantageous properties of the hollow particles of formula according to the invention are not, or are not substantially, adversely affected by the envisaged addition.

The compositions according to the invention may be applied directly to the skin or, alternatively, to cosmetic supports of occlusive or non-occlusive type, intended to be applied locally to the skin. By way of non-limiting examples of cosmetic supports, mention may particularly be made of a patch, a wipe, a roll-on and a pen. The compositions of this type may be in the form of a facial and/or body care or makeup product, and may be packaged, for example, in the form of a cream in a jar or of a fluid in a tube or a pump-action bottle.

The composition according to the present invention will comprise, according to one particular embodiment, in addition to the hollow particles, at least one additional active agent for the care of oily or oily-prone skin.

Additional Active Agents for the Care of Oily Skin

In the context of the present invention, the expression "additional active agent for the care of oily skin" is understood to mean a compound which has on its own, i.e. not requiring the intervention of an external agent to activate it, a biological activity which may be in particular:

a desquamating activity, and/or
an antimicrobial activity, and/or
a soothing or anti-inflammatory activity, and/or
a sebum-regulating activity, and/or
an antioxidant activity, and/or
a healing activity, and/or
an astringent activity.

The additional active agent for the care of oily skin that may be used in the compositions of the invention is preferentially chosen from desquamating agents, antimicrobial agents, soothing agents, anti-inflammatory agents sebum-regulating agents, antioxidants, healing agents, astringents, and mixtures thereof.

The term "sebum-regulating agent" or "anti-seborrhoeic agent" is understood to mean in particular agents capable of regulating the activity of the sebaceous glands.

The term "antimicrobial agents" is understood to mean agents that have effects on the specific flora of oily skin, such as, for example, *P. acnes*. These effects may be either bactericidal, or effects that act against bacterial adhesion (that prevent and/or reduce the adhesion of microorganisms), or effects that act on the biofilm of the bacteria so as to prevent multiplication thereof.

The term "desquamating agent" is understood to mean any compound capable of acting either directly on desquamation by promoting exfoliation, or on the enzymes involved in desquamation or the degradation of corneodesmosomes, glycosidases, stratum corneum chymotryptic enzyme (SCCE), or even other proteases (trypsin, chymotrypsin-like).

The term "antioxidant" is understood to mean agents having an antioxidant activity (which prevent the oxidation of squalene and the formation of comedones).

According to the invention, the term "astringents" is understood to mean agents for combating the dilation of the sebaceous follicles.

The additional active agent for the care of oily skin that is used in the composition according to the invention may represent from 0.0001% to 20%, preferably from 0.01% to 10% and even better still from 0.01% to 5% by weight relative to the total weight of the composition.

According to one embodiment, a composition according to the invention will not comprise essential oil.

It is a matter of routine for those skilled in the art to adjust the nature and amount of the additives present in the compositions in accordance with the invention such that the desired cosmetic properties thereof are not thereby affected.

It will also be possible to apply to the skin, in particular before steps a) and b), a cleansing product such as Cetaphil (water, cetyl alcool, propylene glycol, sodium lauryl sulfate, stearyl alcohol, methylparaben, propylparaben, butylparaben). The product applied may be relatively mild, making it possible to only gently cleanse the skin, for example to remove makeup, but not being a product that is too degreasing.

DETAILED DESCRIPTION

The invention will be better understood on reading the following detailed description of exemplary embodiments of the invention and on examining the appended drawing, in which.

DEVICE

Figure 1:
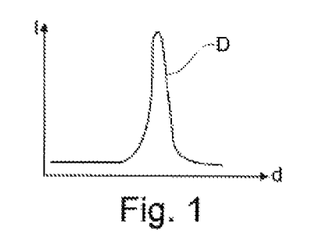
FIGS. 1 to 3 illustrate light spectra (Intensity I as a function of the wavelength λ) emitted in accordance with the invention.

The method according to the invention is, for example, carried out by means of a device for applying light to the skin, comprising at least one source of quasi-monochromatic light of artificial origin making it possible to emit the first wavelength D, as illustrated in FIG. 1, and one or more exit window(s) for the light emitted.

Figure 2:
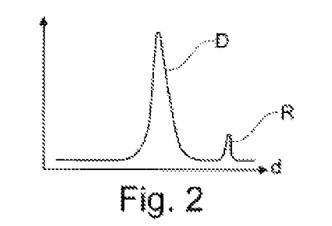

The device may also be configured to emit a second quasi-monochromatic light of artificial origin having a wavelength peak R between 700 and 1000 nm, better still between 800 and 900 nm, for example of the order of around 870 nm, as illustrated in FIG. 2. This light is a red or infrared light. The source of red or infrared light may be the same as or different from that behind the first light mentioned above. The device may comprise a single light source configured to emit two different quasi-monochromatic lights. As a variant, the device may comprise two different sources that each emit at least one different quasi-monochromatic light, it being possible for the two sources to be activated simultaneously or successively.

Figure 3:
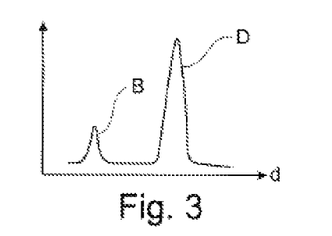

The device may also be configured to emit a third additional quasi-monochromatic light of artificial origin, having a peak B of wavelength, for example, between 400 and 450 nm, in particular of the order of 410 to 420 nm, as illustrated in FIG. 3. This light is a blue light. The device may comprise an additional light source different from the light source(s) emitting the first light D and the red or infrared light R.

Figure 4:
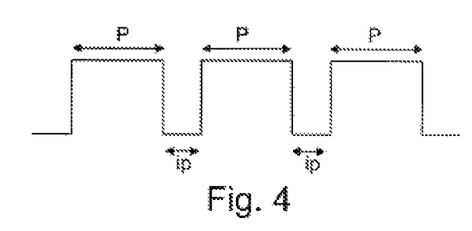
FIG. 4 illustrates a sequence of pulses in accordance with one exemplary embodiment of the invention.

The device may be configured to emit a pulsed light with pulses having a duration p of between 100 and 500 ms, better still between 200 and 300 ms, for example of the order of 250 ms, and interpulse intervals ip having a duration of between 50 and 200 ms, better still between 70 and 150 ms, for example of the order of 100 ms, as illustrated in FIG. 4. As a variant, the device may be configured to emit a continuous light.

The surface power density of the light emitted may be less than 40 mW/cm$^2$, preferably between 1 and 20 mW/cm$^2$, better still between 1 and 10 mW/cm$^2$.

The surface energy density emitted may be less than 4 J/cm$^2$, better still between 20 mJ/cm$^2$ and 1 J/cm$^2$, for example of the order of 175 mJ/cm$^2$.

The device may be configured to emit light over a certain predefined operating period, then to switch off automatically. The operating period may be less than 20 minutes, for example between 20 and 100 seconds, for example of the order of 35 seconds or 70 seconds in certain exemplary embodiments.

The device may be configured so that the power of the dominant peak of the light R is at least less than a quarter of the power of the dominant peak of the light D.

The device may comprise means for conducting the light emitted by the source close to the skin, for example one or more optical fibres. The device may comprise a bundle of optical fibres conducting the light emitted by the source to a plurality of regions of the skin to be treated.

The device may be configured to make it possible to treat all of the subject's skin to be treated in a static manner. It may, for example, take the form of a helmet intended to cover the head, in order to enable treatment of the oily scalp. It may, as a variant, comprise several panels, each panel bearing one or more light sources, intended to be positioned in front of the face and at the sides of the face of a subject.

The device may comprise reliefs intended to be placed in contact with the skin of the subject when the device is placed on the subject in order to carry out the treatment, these reliefs making it possible to guarantee an adequate distance between the skin to be treated and the light source(s).

As a variant, the device comprises two curved LED panels that pivot relative to one another, a height-adjustable arm, a control unit and a power supply system. Each panel may consist of a matrix of at least 1000 LEDs.

As a variant, the device comprises a single curved LED panel connected to a control unit and to a power supply system. Each panel may consist of a matrix of at least 800 LEDs.

Test

A test was carried out using a GentleWaves™ LED device from the company Light Bioscience emitting at a dominant wavelength of around 595 nm (visible yellow light) and also at a second wavelength of 870 nm, at a lower power, with a total surface power density of 5 mW/cm$^2$, the light being pulsed with a cycle of 250 ms of emission and 100 ms between the emissions. The power of the wavelength at 870 nm represents at most 10% to 15% of the power of the dominant wavelength at 595 nm.

This test was carried out on 31 Caucasian women in good health with oily skin (18-50 years old, Sebumeter® score greater than 125 μm/cm$^2$, Sebutape® score greater than 2). The subjects are treated with the light on one half of the face taken randomly, once a day, five consecutive days out of seven, for two weeks, the sessions having a duration of 70 s. Following the treatment with the light and on all the other days, the subjects apply, to the whole of the face, composition A of the table below, which is a foundation. Unless otherwise mentioned, the amounts indicated are expressed as weight percentages.

Composition A

| Raw materials | % by weight |
|---|---|
| Water | 65.55 |
| Propylene glycol | 2.00 |
| Glycerol | 7.00 |
| Red 4 | 0.0001 |
| Water | 0.0999 |
| Ammonium polyacryloyldimethyl taurate (1) | 1.00 |
| Polydimethylsiloxane (viscosity: 10 CTS) (2) | 7.00 |
| Polydimethylsiloxane comprising propyl groups, polyoxyethylenated | 0.70 |
| Polydimethylsiloxane (viscosity: 5 CTS) (3) | 4.00 |
| Polysaccharide rich in fucose (20%) at 1.1% in stabilised water (1.5% phenoxyethanol) (4) | 2.00 |
| Silica silylate | 2.00 |
| Caprylyl glycol | 0.40 |
| Menthol | 0.05 |
| Denatured alcohol | 8.00 |
| Fragrance | 0.20 |

(1) HOSTACERIN AMPS from CLARIANT
(2) XIAMETER PMX-200 SILICONE FLUID 10CS from DOW CORNING
(3) XIAMETER PMX-200 SILICONE FLUID 50S from DOW CORNING
(4) FUCOGEL 1.5P from SOLABIA In total, the subjects receive 9 treatments with the lights (days 1 to 5 and 8 to 11) and 11 treatments with the composition (days 1 to 11). There is no treatment on the twelfth day. An evaluation visit is carried out on the first day before the treatments (Baseline) and on the twelfth day (T2w).

Shininess of the Skin

Figure 5:
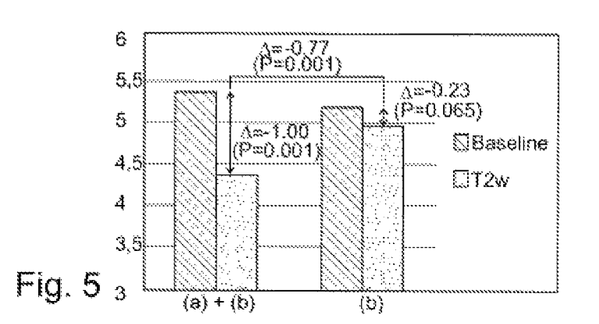
FIGS. 5 to 7 illustrate the values of the means of the results obtained in a test carried out in accordance with the invention.

The results of the evaluation, by an evaluator, of the shininess of the skin have been illustrated in FIG. 5 and in the table below. The evaluation is carried out blind, by an expert, for each of the halves of the face, with a mark being given on a ten-point scale.

| Parameter | Treatment | Evaluation | Mean | SD | Variation of the mean | in % | P of the variation of the mean |
|---|---|---|---|---|---|---|---|
| Shininess of the skin | (a) + (b) | Baseline | 5.39 | ±1.02 | −1.00 | −18.56 | <0.001 |
| | | T2 w | 4.39 | ±0.84 | | | |
| | (b) | Baseline | 5.23 | ±1.09 | −0.23 | −4.32 | 0.065 |
| | | T2 w | 5.00 | ±0.93 | | | |

The combination of the treatment with the light and with the composition shows an improvement of 1 point in the shininess, on the ten-point scale, compared with the initial shininess. The effect remains even 24 h after the final treatment. In addition, the effect is 0.77 points better for the treatment according to the invention, comprising the combination of treatment (a) with the light and (b) with the composition, compared with a treatment (b) with the composition alone.

Moreover, an analysis using VISIA 2D with the software from the company Stephen & Ass is carried out on the photos of the half-faces, in order to measure the shininess value L* thereon.

| Parameter | Treatment | Evaluation | Mean | SD | Variation of the mean | P of the variation of the mean |
|---|---|---|---|---|---|---|
| L* (Shininess) | (a) + (b) | Baseline | 233.64 | ±5.46 | −1.65 | 0.009 |
| | | T2 w | 231.99 | ±5.68 | | |
| | (b) | Baseline | 233.21 | ±5.39 | −0.53 | 0.541 |
| | | T2 w | 232.68 | ±5.18 | | |

These results statistically confirm the analysis carried out by the evaluator.

Dermascore® Results

The Dermascore values after 2 weeks of treatment were compared to the Dermascore values before treatment. They are given in the table below and illustrated in FIG. 6.

Figure 6:
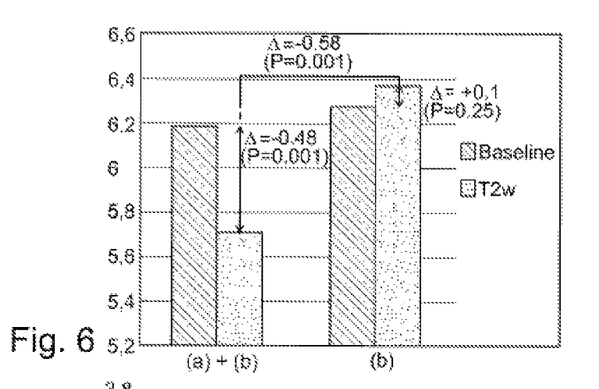

| Parameter | Treatment | Evaluation | Mean | SD | Variation of the mean | in % | P of the variation of the mean |
|---|---|---|---|---|---|---|---|
| Pore size (Dermascore) | (a) + (b) | Baseline | 6.19 | 1.11 | −0.48 | −7.81 | <0.001 |
| | | T2 w | 5.71 | 1.49 | | | |
| | (b) | Baseline | 6.29 | 1.01 | 0.10 | 1.54 | 0.250 |
| | | T2 w | 6.39 | 1.02 | | | |

When the treatment a)+b) is applied, in accordance with the invention, an improvement in the score of 0.48 point on an 8-point scale is obtained, i.e. a total difference of 0.58 point in favour of the treatment a)+b) in accordance with the invention.

It should be noted that the measurement of the effect of treatment b) alone is not significant, insofar as the evaluation is carried out 24 h after the final treatment.

Sebutape® Results

The Sebutape values after 2 weeks of treatment were compared to the Sebutape values before treatment. They are given in the table below and illustrated in FIG. 7.

Figure 7:
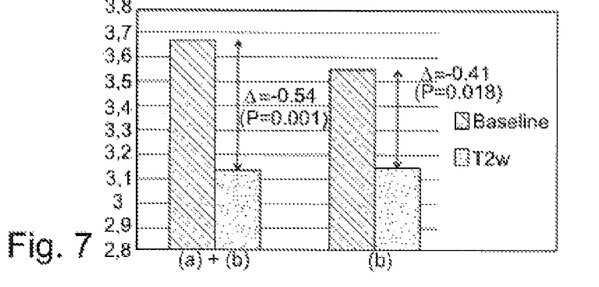

| Parameter | Treatment | Evaluation | Mean | SD | Variation of the mean | in % | P of the variation of the mean |
|---|---|---|---|---|---|---|---|
| Shininess of the skin | (a) + (b) | Baseline | 3.68 | ±0.78 | −0.54 | −14.74 | 0.001 |
| | | T2 w | 3.14 | ±0.93 | | | |
| | (b) | Baseline | 3.57 | ±0.84 | −0.41 | −11.55 | 0.018 |
| | | T2 w | 3.16 | ±0.98 | | | |

For the two treatments, a statistically significant improvement in the score, on a scale of 1 to 5, is obtained in two weeks.

Thus, the combination of treatments a) and b) in accordance with the invention makes it possible to obtain an improvement in the appearance of oily skin in terms of shininess and pore size with a persistent efficacy. Both an immediate effect and a longer-term effect are obtained. In addition, the daily treatment is easy to apply.

The invention is not limited to the exemplary embodiments that have just been described.

The expression "comprising a" should be understood as being synonymous with "comprising at least one".

The invention claimed is:

1. Method for the cosmetic (non-therapeutic) treatment of oily skin, comprising:
   a) exposing the oily skin to a first quasi-monochromatic light of artificial origin having a dominant wavelength peak between 300 and 700 nm, and
   b) applying to the oily skin a cosmetic composition comprising at least 1% by weight of hollow particles and, relative to the total weight of said composition, the hollow particles being hydrophobic silica aerogel particles.

2. Method according to claim 1, in which the oily skin is also exposed, to a second quasi-monochromatic light of artificial origin having a dominant wavelength peak between 700 and 1000 nm.

3. Method according to claim 1, in which said light, is pulsed with pulses having a duration of between 100 and 500 ms, and/or with interpulse intervals having a duration of between 50 and 200 ms.

4. Method according to claim 1, in which the light received by the oily skin has a surface power density of less than or equal to 40 mW/cm$^2$.

5. Method according to claim 1, in which the light source(s) comprise(s) at least one of the following: an LED, an LED matrix, an OLED, a laser, an incandescent lamp equipped with a dichroic filter, and a quasi-monochromatic LED.

6. Method according to claim 1, in which the hydrophobic silica aerogel particles have a specific surface area per unit of mass ($S_M$) of greater than 600 m$^2$/g.

7. Method according to claim 1, in which the hydrophobic silica aerogel particles have a size, expressed as the volume average diameter (D[0.5]), ranging from 5 to 30 μm.

8. Method according to claims 1, in which the hydrophobic silica aerogel particles have a tapped density ρ ranging from 0.04 g/cm$^3$ to 0.10 g/cm$^3$.

9. Method according to claim 1, in which the hydrophobic silica aerogel particles have an oil-absorbing capacity, measured at the wet point, ranging from 5 to 18 ml/g of particles.

10. Method according to claim 1, in which the hydrophobic silica aerogel particles are surface-modified with trimethylsilyl groups.

11. Method according to claim 1, in which the composition comprises water and/or a water-soluble solvent.

12. Method according claim 1, in which the composition comprises a water content of greater than 30% by weight.

13. Method according to claim 1, in which the composition is in the form of an emulsion obtained by dispersion of a fatty phase, in an aqueous phase.

14. Method according to claim 1, in which the hydrophobic silica aerogel particles are of silylated silica type.

15. Method according to claim 1, in which the silica particles have been surface-treated with silylating agents.

* * * * *